United States Patent [19]

Linker et al.

[11] Patent Number: 6,159,903
[45] Date of Patent: Dec. 12, 2000

[54] SUBSTITUTED 2-ARYL-1,2,4-TRIAZINE-3,5-DI(THI)ONES AS HERBICIDES

[75] Inventors: Karl-Heinz Linker; Kurt Findeisen, both of Leverkusen, Germany; Markus Dollinger, Knox, Kans.; Hans-Joachim Santel, Leverkusen, Germany

[73] Assignee: Bayer Aktiengesellschaft, Leverkusen, Germany

[21] Appl. No.: 09/125,278

[22] PCT Filed: Feb. 10, 1997

[86] PCT No.: PCT/EP97/00610

§ 371 Date: Aug. 14, 1998

§ 102(e) Date: Aug. 14, 1998

[87] PCT Pub. No.: WO97/30980

PCT Pub. Date: Aug. 28, 1997

[30] Foreign Application Priority Data

Feb. 22, 1996 [DE] Germany ............. 196 06 594

[51] Int. Cl.[7] ............. A01N 43/707; C07D 253/075
[52] U.S. Cl. ............. 504/229; 544/182; 548/262.2
[58] Field of Search ............. 544/182; 504/229

[56] References Cited

U.S. PATENT DOCUMENTS 4,956,004  9/1990  Thiodoridis ............. 544/182

FOREIGN PATENT DOCUMENTS 0 011 693   6/1980   European Pat. Off. .
2149645    9/1972   Germany .
WO 86/00072 1/1986   WIPO .

*Primary Examiner*—Mukund J. Shah
*Assistant Examiner*—Venkataraman Balasubramanian
*Attorney, Agent, or Firm*—Norris, McLaughlin & Marcus, P.A.

[57] ABSTRACT

The invention relates to novel 2-aryl-1,2,4-triazine-3,5-di(thi)ones of the general formula (I),

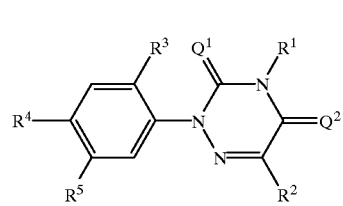

in which $R^1$, $R^2$, $R^3$, $R^4$, $R^5$, $Q^1$ and $Q^2$ are each as defined in the description, to processes for their preparation and to their use as herbicides.

5 Claims, No Drawings

SUBSTITUTED 2-ARYL-1,2,4-TRIAZINE-3,5-DI(THI)ONES AS HERBICIDES

The invention relates to novel substituted 2-aryl-1,2,4-triazine-3,5-di(thi)ones, to processes for their preparation and to their use as herbicides.

EP 11693, EP 271170, WO 86/00072, U.S. Pat. No. 4,755,217, U.S. Pat. No. 4,878,941, U.S. Pat. No. 4,956,004, U.S. Pat. No. 5,262,390, and U.S. Pat. No. 5,344,812 disclose that certain substituted 2-aryl-1,2,4-triazine-(thi) ones have herbicidal properties. However, the compounds described therein have not attained any major importance.

This invention, accordingly, provides the novel substituted 2-aryl-1,2,4-triazine-3,5-di(thi)ones of the general formula (I),

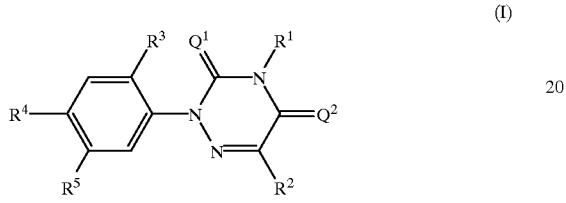

in which $Q^1$ represents oxygen or sulphur, $Q^2$ represents oxygen or sulphur, $R^1$ represents hydrogen, cyano, amino, or represents respectively optionally substitutued alkyl, alkoxy, alkylamino, dialkylamino, alkylcarbonyl, alkoxycarbonyl, alkenyl, alkenylcarbonyl, alkenyloxycarbonyl, alkinyl, alkinylcarbonyl, alkinyloxycarbonyl, cycloalkyl or cycloalkylalkyl, $R^2$ represents hydrogen, halogen, nitro, carboxyl, cyano, thiocarbamoyl, amino, or represents respectively optionally substituted alkyl, alkoxy, alkylthio, alkylamino, dialkylamino, alkenyl, alkenyloxy, alkenylthio, alkinyl, alkinyloxy, alkinylthio, cycloalkyl or cycloalkylalkyl, $R^3$ represents halogen, $R^4$ represents cyano or thiocarbamoyl and $R^5$ represents the grouping below,

in which $A^1$ represents a single bond, represents oxygen, sulphur, —SO—, —SO$_2$—, —CO— or the grouping —N—A$^4$—, where A$^4$ represents hydrogen, hydroxyl, alkyl, alkenyl, alkinyl, alkoxy, aryl, alkylcarbonyl, arylcarbonyl, alkylsulphonyl or arylsulphonyl, $A^1$ furthermore represents respectively optionally halogen-substituted alkanediyl, alkenediyl, azaalkenediyl, alkinediyl, cycloalkanediyl, cycloalkenediyl or phenylene, $A^2$ represents a single bond, represents oxygen, sulphur, —SO—, —SO$_2$—, —CO— or the grouping —N—A$^4$—, where A$^4$ represents hydrogen, hydroxyl, alkyl, alkoxy, aryl, alkylsulphonyl or arylsulphonyl, $A^2$ furthermore represents respectively optionally halogen-substituted alkanediyl, alkenediyl, azaalkenediyl, alkinediyl, cycloalkanediyl, cycloalkenediyl or phenylene, $A^3$ represents hydrogen with the proviso that in this case $A^1$ and/or $A^2$ do not represent a single bond $A^3$ furthermore represents hydroxyl, mercapto, amino, cyano, isocyano, thiocyanato, nitro, carboxyl, carbamoyl, thiocarbamoyl, sulpho, chlorosulphonyl, halogen, represents respectively optionally halogen- or alkoxy-substituted alkyl, alkoxy, alkylthio, alkylsulphinyl, alkylsulphonyl, alkylamino, dialkylamino, alkoxycarbonyl or dialkoxy(thio) phosphoryl, represents respectively optionally halogen-substituted alkenyl, alkenyloxy, alkenylthio, alkenylamino, alkylideneamino, alkenyloxycarbonyl, alkinyl, alkinyloxy, alkinylthio, alkinylamino or alkinyloxycarbonyl, represents respectively optionally halogen-, cyano-, carboxyl-, alkyl- and/or alkoxy-carbonyl-substituted cycloalkyl, cycloalkyloxy, cycloalkylalkyl, cycloalkylalkoxy, cycloalkylideneamino, cycloalkyloxy-carbonyl or cycloalkylalkoxy-carbonyl, or represents respectively optionally nitro-, cyano-carboxyl-, halogen-, alkyl-, halogenalkyl-, alkyloxy-, halogenalkyloxy- and/or alkoxy-carbonyl-substituted aryl, aryloxy, aralkyl, arylalkoxy, aryloxycarbonyl or arylalkoxycarbonyl, $A^3$ furthermore represents respectively optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolylalkyl, furylalkyl, thienylalkyl, oxazolylalkyl, isoxazolylalkyl, thiazolylalkyl, pyridinylalkyl, pyrimidinylalkyl, pyrazolylalkoxy, furylalkoxy, represents perhydro-pyranylalkoxy or pyridylalkoxy.

The novel substituted 2-aryl-1,2,4-triazine-3,5-di(thi) ones of the general formula (I), are obtained when (a) 1,2,4-triazine-3,5-di(thi)ones of the general formula (II),

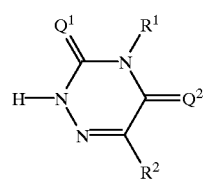

in which $Q^1$, $Q^2$, $R^1$ and $R^2$ are each as defined above, are reacted with halogenobenzene derivatives of the general formula (III),

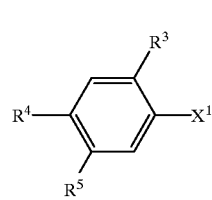

in which $R^3$, $R^4$ and $R^5$ are each as defined above and $X^1$ represents halogen, if appropriate in the presence of a diluent and if appropriate in the presence of a reaction auxiliary, or when (b) 2-aryl-1,2,4-triazine-3,5-di(thi)ones of the general formula (Ia),

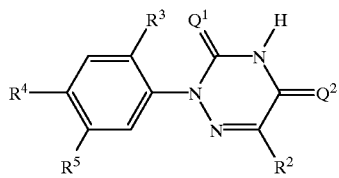
(Ia)

in which

Q$^1$, Q$^2$, R$^2$, R$^3$, R$^4$ and R$^5$ are each as defined above are reacted with alkylating agents of the general formula (IV),

(IV)

in which

R$^1$ is as defined above and

X$^2$ represents halogen or the grouping —O—SO$_2$—O—R$^1$, if appropriate in the presence of a diluent and if appropriate in the presence of a reaction auxiliary, or when (c) arylhydrazones of the general formula (V),

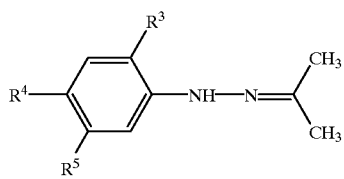
(V)

in which

R$^3$, R$^4$ and R$^5$ are each as defined above are reacted with alkali metal (thio)cyanates of the general formula (VI),

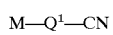
(VI)

in which

Q$^1$ is as defined above and

M represents an alkali metal atom, if appropriate in the presence of a diluent and if appropriate in the presence of a reaction auxiliary and the resulting 2-aryl-1,2,4-triazolidine-3-(thi)ones of the general formula (VII),

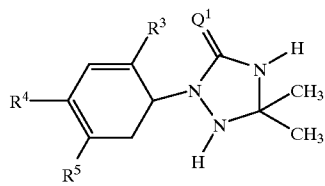
(VII)

in which

Q$^1$, R$^3$, R$^4$ and R$^5$ are each as defined above are reacted with ketocarboxylic acids of the general formula (VIII),

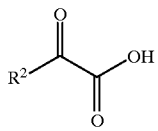
(VIII)

in which

R$^2$ is as defined above if appropriate in the presence of a diluent and if appropriate in the presence of a reaction auxiliary, or when (d) aryl-amines of the general formula (IX),

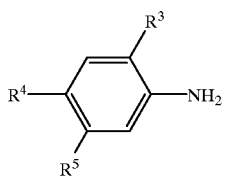
(IX)

in which

R$^3$, R$^4$ and R$^5$ are each as defined above are diazotized and subsequently reacted with a cyanoacetylcarbamic acid ester of the general formula (X),

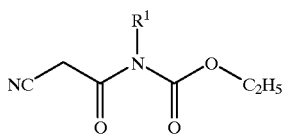
(X)

in which

R$^1$ is as defined above, if appropriate in the presence of a diluent and if appropriate in the presence of a reaction auxiliary, and the resulting compounds of the general formula (XI),

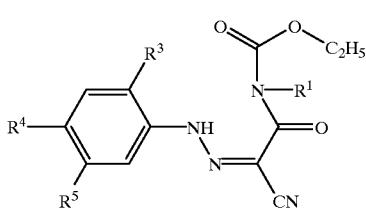
(XI)

in which

R$^1$, R$^3$, R$^4$ and R$^5$ are each as defined above are cyclized if appropriate in the presence of a diluent and if appropriate in the presence of a reaction auxiliary, or when (e) arylhydrazines of the general formula (XII)

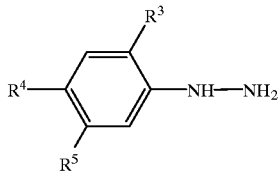

(XII)

in which $R^3$, $R^4$ and $R^5$ are each as defined above are reacted with ketocarboxylic acid derivatives of the general formula (XIII),

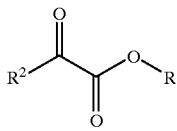

(XIII)

in which $R^2$ is as defined above and

R represents hydrogen or alkyl, if appropriate in the presence of a diluent and if appropriate in the presence of a reaction auxiliary, and the resulting compounds of the general formula (XIV)

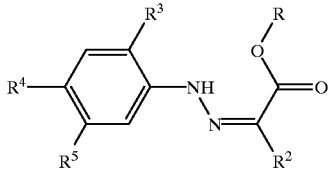

(XIV)

in which $R^2$, $R^3$, $R^4$ and $R^5$ are each as defined above and

R represents hydrogen or alkyl, are reacted with iso(thio)cyanates of the general formula (XV),

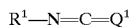

$R^1$—N=C=$Q^1$ (XV)

in which $Q^1$ and $R^1$ are each as defined above, if appropriate in the presence of a diluent and if appropriate in the presence of a reaction auxiliary and the resulting compounds of the general formula (XVI),

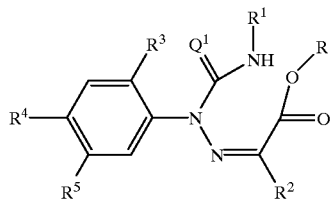

(XVI)

in which $Q^1$, $R^1$, $R^2$, $R^3$, $R^4$ and $R^5$ are each as defined above and R represents hydrogen or alkyl, are cyclized, if appropriate in the presence of a diluent and if appropriate in the presence of a reaction auxiliary, or when (f) 2-aryl-1,2,4-triazine-3,5-dione-6-carboxylic acids of the general formula (XIX),

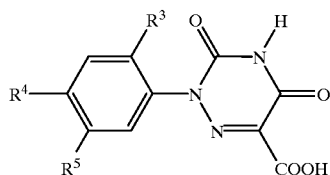

(XIX)

in which $R^3$, $R^4$ and $R^5$ are each as defined above are obtained, if aryl-amines of the general formula (IX),

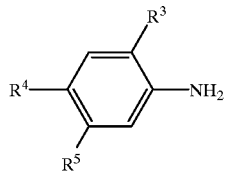

(IX)

in which $R^3$, $R^4$ and $R^5$ are each as defined above are diazotized and subsequently reacted with the malonyldiurethane of the formula (XVII),

$CH_2(CO-NH-COOC_2H_5)_2$ (XVII)

if appropriate in the presence of a diluent and if appropriate in the presence of a reaction auxiliary and subsequently cyclized.

It is also possible to convert the compounds of the general formula (I) according to further customary methods into other compounds of the general formula (I) according to the definition above, for example by nucleophilic substitution (for example $R^5$: F→OH, SH, $NH_2$, $OCH_3$, $OCH_2CH=CH_2$, $NHSO_2CH_3$); or by further functional group conversions (for example $R^2$: COOH→H, COOH→COCl, $COOCH_3$, COCl→$CONH_2$, CN→$CSNH_2$; $R^4$: CN→$CSNH_2$; $R^5$: $NO_2$→$NH_2$, $NH_2$→F, Cl, Br, CN, $NHSO_2CH_3$, $SO_2Cl$) or by oxidation or sulphurization (for example $Q^1$, $Q^2$: O→S, or S→O), cf. also the Preparation Examples.

The novel substituted 2-aryl-1,2,4-triazine-3,5-di(thi)ones of the general formula (I) have strong and selective herbicidal activity.

In the definition, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which $Q^1$ represents oxygen or sulphur, $Q^2$ represents oxygen or sulphur, $R^1$ represents hydrogen, cyano, amino, represents respectively optionally cyano-fluorine-, chlorine-, $C_1$–$C_4$-alkoxy- or $C_1$–$C_4$-alkylthio-substituted alkyl, alkoxy, alkylamino, dialkylamino, alkylcarbonyl or alkoxycarbonyl having in each case 1 to 6 carbon atoms in the alkyl groups, represents respectively optionally fluorine-, chlorine- or bromine-substituted alkenyl, alkenylcarbonyl, alkenyloxycarbonyl, alkinyl, alkinylcarbonyl or alkinyloxycarbonyl having in each case 2 to 6 carbon atoms in the alkenyl or alkinyl groups, or represents respectively optionally cyano-, fluorine-, chlorine-, bromine- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety, $R^2$ represents hydrogen, halogen, nitro, carboxyl, cyano, thiocarbamoyl, amino, represents respectively optionally cyano-, fluorine-, chlorine-, $C_1$–$C_4$-alkoxy- or $C_1$–$C_4$-alkylthio-substituted alkyl, alkoxy, alkylthio, alkylamino or dialkylamino having in each case 1 to 6 carbon atoms in the alkyl groups, represents respectively optionally fluorine-, chlorine- or bromine-substituted alkenyl, alkenyloxy, alkenylthio, alkinyl, alkinyloxy or alkinylthio having in each case 2 to 6 carbon atoms in the alkenyl- or alkinyl-groups, or represents respectively optionally cyano-, fluorine-, chlorine-, bromine- or $C_1$–$C_4$-alkyl-substituted cycloalkyl or cycloalkylalkyl having in each case 3 to 6 carbon atoms in the cycloalkyl groups and optionally 1 to 6 carbon atoms in the alkyl moiety, $R^3$ represents fluorine, chlorine or bromine, $R^4$ represents cyano or thiocarbamoyl and $R^5$ represents the grouping —$A^1$—$A^2$—$A^3$, in which $A^1$ represents a single bond, represents oxygen, sulphur, —SO—, —$SO_2$—, —CO— or the grouping —N—$A^4$—, where $A^4$ represents hydrogen, hydroxyl, $C_1$–$C_4$-alkyl, $C_3$–$C_4$-alkenyl, $C_3$–$C_4$-alkinyl, $C_1$–$C_4$-alkoxy, phenyl, $C_1$–$C_4$-alkylsulphonyl or phenylsulphonyl, $A^1$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^2$ represents a single bond, represents oxygen, sulphur, —SO—, -$SO_2$—, —CO— or the grouping —N—$A^4$—, where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl, $A^2$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^3$ represents hydrogen, with the proviso that in this case $A^1$ and/or $A^2$ do not represent a single bond, $A^3$ furthermore represents hydroxyl, amino, cyano, isocyano, thiocyanato, nitro, carboxyl, carbamoyl, thiocarbamoyl, sulpho, chlorosulphonyl, fluorine, chlorine, bromine, represents respectively optionally fluorine-, chlorine- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy-(thio)phosphoryl having in each case 1 to 6 carbon atoms in the alkyl groups, represents respectively optionally fluorine- or chlorine-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, represents respectively optionally fluorine-, chlorine-, cyano-, carboxyl-, $C_1$–$C_4$-alkyl- and/or $C_1$–$C_4$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, or represents respectively optionally nitro-cyano-, carboxyl-, fluorine-, chlorine-, bromine-, $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxy-carbonyl-substituted phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, $A^3$ furthermore represents respectively optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazolyl-$C_1$–$C_4$-alkyl, thiazolyl-$C_1$–$C_4$-alkyl, pyridinyl-$C_1$–$C_4$-alkyl, pyrimidinyl-$C_1$–$C_4$-alkyl, pyrazolylmethoxy, furylmethoxy, represents perhydropyranylmethoxy or pyridylmethoxy.

The invention in particular relates to compounds of the formula (I), in which $Q^1$ represents oxygen or sulphur, $Q^2$ represents oxygen or sulphur, $R^1$ represents hydrogen, cyano, amino, represents respectively optionally cyano-, fluorine-, chlorine-, methoxy- or ethoxy-substituted methyl, ethyl, n- or i-propyl, n-, i- s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, acetyl, propionyl, n- or i-butyroyl, methoxycarbonyl, ethoxycarbonyl, n- or i-propoxycarbonyl, represents respectively optionally fluorine-, chlorine- or bromine-substituted propenyl, butenyl, propenylcarbonyl, butenylcarbonyl, propenyloxycarbonyl, butenyloxycarbonyl, represents propinyl, butinyl, propinylcarbonyl, butinylcarbonyl, propinyloxycarbonyl or butinyloxycarbonyl, or represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, $R^2$ represents hydrogen, halogen, nitro, carboxyl, cyano, thiocarbamoyl, amino, represents respectively optionally cyano-, fluorine-, chlorine-, methoxy- or ethoxy-substituted methyl, ethyl, n- or i-propyl, n-, i- s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents respectively optionally fluorine-, chlorine- or bromine-substituted propenyl, propenyloxy, propenylthio, butenyl, butenyloxy or butenylthio, represents propinyl, propinyloxy, propinylthio, butinyl, butinyloxy or butinylthio, or represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, $R^3$ represents fluorine or chlorine, $R^4$ represents cyano or thiocarbamoyl and $R^5$ represents the grouping —$A^1$—$A^2$—$A^3$,
in which
$A^1$ represents a single bond, represents oxygen, sulphur, —SO—, —$SO_2$—, —CO— or the grouping —N—$A^4$—, where $A^4$ represents hydrogen, hydroxyl, methyl, ethyl, n- or i-propyl, methoxy, ethoxy, n- or i-propoxy, methylsulphonyl or ethylsulphonyl, $A^1$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl, $A^2$ represents a single bond, represents oxygen, sulphur, —SO—, —$SO_2$—, —CO— or the grouping —N—$A^4$—, where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, $A^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl, $A^3$ represents hydrogen, with the proviso that in this case $A^1$ and/or $A^2$ do not represent a single bond, $A^3$ furthermore represents hydroxyl, amino, cyano, nitro, carboxy, carbamoyl, sulpho, fluorine, chlorine, bromine, represents respectively optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl or dipropoxyphosphoryl, diisopropoxyphosphoryl, represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, represents respectively optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexyl-ideneamino, cyclopentyloxycarbonyl, cyclohexyloxycarbonyl, cyclopentylmethoxycarbonyl or cyclohexylmethoxycarbonyl, or represents respectively optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, $A^3$ furthermore represents (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolylmethyl, thiazolylmethyl, pyridinylmethyl, pyrimidinylmethyl, pyrazolylmethoxy, furylmethoxy or pyridylmethoxy.

The general or preferred radical definitions listed above apply both to the end products of the formula (I) and, in a corresponding manner, also to the starting materials or intermediates which are required in each case for the preparation. These radical definitions can be combined with each other at will, i.e. combinations between the given preferred ranges are also possible.

Examples of the compounds of the formula (I) according to the invention are listed in the groups below.

Group 1

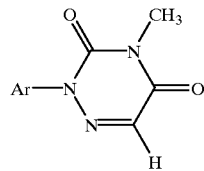

(IA-1)

Ar has in this case for example the meanings given below:
2-fluoro-5-chloro-4-cyano-phenyl, 2,5-dichloro-4-cyano-phenyl, 2-chloro-5-fluoro-4-cyano-phenyl, 2-chloro-4,5-dicyano-phenyl, 2,5-difluoro-4-cyano-phenyl, 2-chloro-4-cyano-5-methyl-phenyl, 2-fluoro-4-cyano-5-methyl-phenyl, 2-chloro-4-cyano-5-tri-fluoromethyl-phenyl, 2-fluoro-4-cyano-5-trifluoro-methyl-phenyl, 2,5-difluoro-4-thio-carbamoyl-phenyl, 2-fluoro-4-cyano-5-methoxy-phenyl, 2-fluoro-4-cyano-5-i-propoxy-phenyl, 2-chloro-4-cyano-5-(2-propinyloxy)-phenyl, 2-fluoro-4-cyano-5-(1-methyl-2-propinyloxy)-phenyl, 2-chloro-4-thiocarbamoyl-5-i-propoxy-phenyl, 2-fluoro-4-cyano-5-

(2-propenyloxy)-phenyl, 2-chloro-4-cyano-5-methylsulphonyl-amino-phenyl, 2-fluoro-4-cyano-5-ethylsulphonylamino-phenyl, 2-fluoro-4-thio-carbamoyl-5-methylsulphonyl-phenyl, 2-chloro-4-cyano-5-ethylsulphonylamino-phenyl, 2-fluoro-4-cyano-5-cyclopropylsulphonylamino-phenyl, 2-fluoro-4-cyano-5-i-propylsulphonylamino-phenyl, 2-chloro-4-thiocarbamoyl-5-ethylsulphonylamino-phenyl, 2-chloro-4-cyano-5-cyano-amino-phenyl, 2-fluoro-4-cyano-5-trifluormethyl-sulphonylamino-phenyl, 2-fluoro-4-cyano-5-(2,2-difluorethylsulphonylamino)-phenyl, 2-fluoro-4-cyano-5-phenylsulphonyl-amino-phenyl, 2-fluoro-4-cyano-5-t-butyl-sulphonylamino-phenyl, 2-chloro-4-cyano-5-methoxycarbonyl-phenyl, 2-fluoro-4-cyano-5-ethoxycarbonyl-phenyl, 2-fluoro-4-thio-carbamoyl-5-methoxycarbonyl-phenyl, 2-chloro-4-cyano-5-(N-cyclopropyl-ethyl-sulphonylamino)-phenyl, 2-fluoro-4-cyano-5-(1-methyl-2-propinylthio)-phenyl, 2-fluoro-4-cyano-5-methylamino-phenyl, 2-chloro-4-thiocarbamoyl-5-methoxycarbonylmethyl-phenyl, 2-chloro-4-cyano-5-(N-methyl-ethylsulphonylamino)-phenyl, 2-chloro-4-cyano-5-i-propoxycarbonyl-phenyl, 2-fluoro-4-cyano-5-(bis-ethylsulphonyl-amino)-phenyl, 2-fluoro-4-cyano-5-(N-methylsulphonyl-ethylsulphonylamino)-phenyl, 2-fluoro-4-cyano-5-(1-methoxy-carbonyl-ethoxy)-phenyl, 2-fluoro-4-cyano-5-cyclo-propyloxy-phenyl, 2-chloro-4 -cyano-5-dimethylamino-phenyl, 2-fluoro-4-cyano-5-tetrahydrofurylmethoxy-phenyl, 2-fluoro-4-cyano-5-amino-phenyl, 2-fluoro-4-cyano-5-methylaminocarbonyl-phenyl, 2-fluoro-4-cyano-5-methylsulphonyloxy-phenyl, 2-chloro-4-cyano-5-difluoro-methoxy-phenyl, 2-fluoro-4-cyano-5-ethoxycarbonylmethoxy-phenyl, 2-fluoro-4-cyano-5-dimethylaminocarbonyl-phenyl, 2-fluoro-4-cyano-5-cyanomethoxy-phenyl, 2-fluoro-4-cyano-5-(2-chloro-2-propenyloxy)-phenyl, 2-fluoro-4-cyano-5-hydroxy-phenyl, 2-fluoro-4-cyano-5-nitro-phenyl, 2-fluoro-4-cyano-5-diethoxyphosphoryl-amino-phenyl, 2-fluoro-4-cyano-5-chlorosulphonyl-phenyl, 2-fluoro-4-cyano-5-formylamino-phenyl, 2-chloro-4-cyano-5-ethoxycarbonyloxy-phenyl, 2-fluoro-4-cyano-5-diethoxyphosphorylmethoxy-phenyl, 2-chloro-4-cyano-5-hydroxy-phenyl, 2-fluoro-4-cyano-5-(N,N-diacetyl-amino)-phenyl, 2-fluoro-4-cyano-5-acetylamino-phenyl, 2-chloro-4-cyano-5-thiocyanato-phenyl, 2-fluoro-4-cyano-5-diethyl-amino-oxy-phenyl, 2-fluoro-4-cyano-5-tetrahydrofuryloxy-phenyl, 2-fluoro-4-cyano-5-ureido-phenyl, 2-fluoro-4-cyano-5-dimethoxymethyleneamino-phenyl, 2-chloro-4-cyano-5-ethoxymethyleneamino-phenyl, 2-fluoro-4-cyano-5-(2-chloro-ethoxy-carbonyl-oxy)-phenyl, 2-chloro-4-cyano-5-dimethylarninomethyleneamino-phenyl, 2-chloro-4-cyano-5-(perhydropyran-4-yloxy)-phenyl, 2-fluoro-4-cyano-5-(2-methoxy-carbonyl-ethyl)-phenyl, 2-chloro-4-cyano-5-(2-carboxy-2-chloro-ethyl)-phenyl, 2-fluoro-4-cyano-5-(2-chloro-2-methoxycarbonyl-ethyl)-phenyl, 2-fluoro-4-cyano-5-(2-chloro-2-s-butoxycarbonyl)-phenyl, 2-fluoro-4-cyano-5-(2-chloro-2-carbamoyl-ethyl)-phenyl, 2-fluoro-4-cyano-5-(2-chloro-2-methoxycarbonyl-1-methyl-ethyl)-phenyl, 2-fluoro-4-cyano-5-(1,2-dibromo-2-methoxycarbonyl-ethyl)-phenyl, 2-chloro-4-cyano-5-(2-chloro-2-i-propoxy-carbonyl-ethyl)-phenyl, 2-fluoro-4-cyano-5-(2-carboxy-2-chloro-ethyl)-phenyl, 2-fluoro-4-cyano-5-(2-chloro-2-ethylaminocarbonyl-ethyl)-phenyl, 2-fluoro-4-cyano-5-(2-allylaminocarbonyl-2-chloro-ethyl)-phenyl, 2-fluoro-4-cyano-5-(2-ethoxycarbonyl-ethenyl)-phenyl, 2-fluoro-4-cyano-5-(2-chloro-2-cyclopropylaminocarbonyl-ethyl)-phenyl, 2-fluoro-4-cyano-5-(2-chloro-2-dimethyl-aminocarbonyl-ethyl)-phenyl, 2-chloro-4-cyano-5-(2-chloro-2-ethylsulphonylamino-carbonyl-ethyl)-phenyl, 2-fluoro-4-thiocarbamoyl-5-(2-ethylaminocarbonyl-ethenyl)-phenyl, 2-fluoro-4-cyano-5-(1-ethoxycarbonyl-ethyl)-phenyl, 2-chloro-4-cyano-5-(1-ethoxycarbonylethyl)-phenyl, 2-chloro-4-cyano-5-carboxy-phenyl, 2-fluoro-4-cyano-5-1-butoxy-phenyl, 2-chloro-4-cyano-5-1-butoxy-phenyl, 2-chloro-4-cyano-5-(2 -methoxy-ethoxy)-phenyl, 2-fluoro-4-cyano-5-(2-oxetanyloxy)-phenyl, 2-fluoro-4-cyano-5-(2-oxetanyloxycarbonylmethoxy)-phenyl, 2-fluoro-4-cyano-5-(2-oxetanyl-oxy)-phenyl.

Group 2

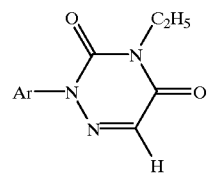

(IA-2)

Ar has in this case the meanings listed above in Group 1.

Group 3

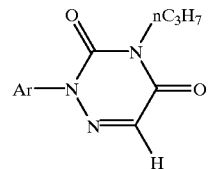

(IA-3)

Ar has in this case the meanings listed above in Group 1.

Group 4

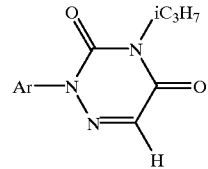

(IA-4)

Ar has in this case the meanings listed above in Group 1.

Group 5

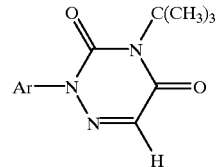

(IA-5)

Ar has in this case the meanings listed above in Group 1.
Group 6

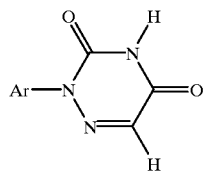
(IA-6)

Ar has in this case the meanings listed above in Group 1.
Group 7

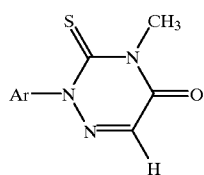
(IA-7)

Ar has in this case the meanings listed above in Group 1.
Group 8

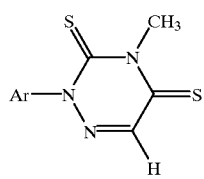
(IA-8)

Ar has in this case the meanings listed above in Group 1.
Group 9

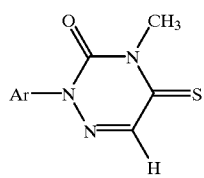
(IA-9)

Ar has in this case the meanings listed above in Group 1.
Group 10

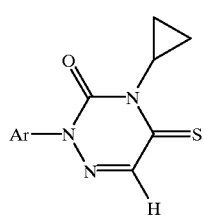
(IA-10)

Ar has in this case the meanings listed above in Group 1.
Group 11

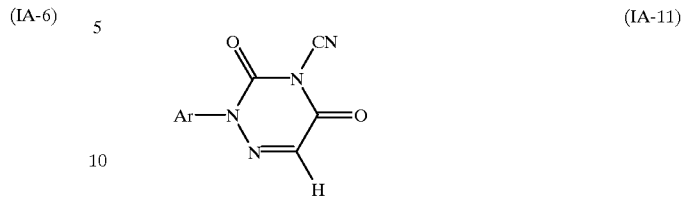
(IA-11)

Ar has in this case the meanings listed above in Group 1.
Group 12

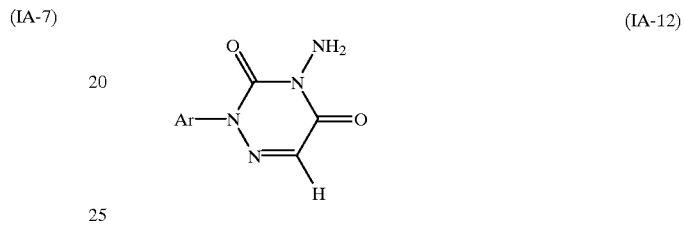
(IA-12)

Ar has in this case the meanings listed above in Group 1.
Group 13

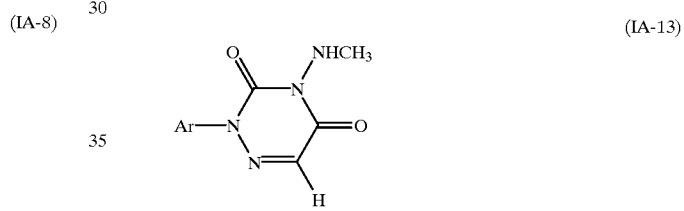
(IA-13)

Ar has in this case the meanings listed above in Group 1.
Group 14

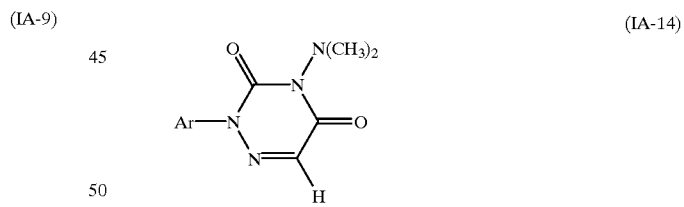
(IA-14)

Ar has in this case the meanings listed above in Group 1.
Group 15

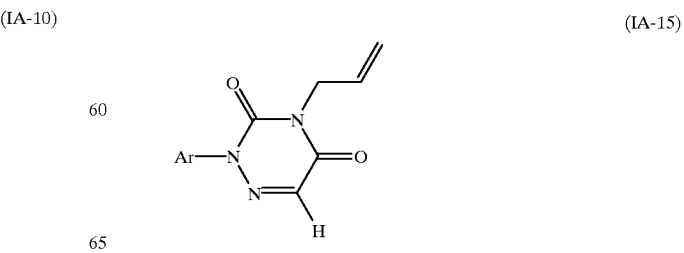
(IA-15)

Ar has in this case the meanings listed above in Group 1.

Group 16

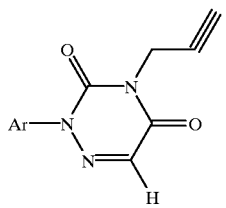
(IA-16)

Ar has in this case the meanings listed above in Group 1.

Group 17

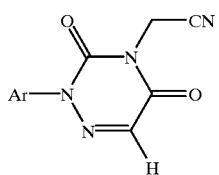
(IA-17)

Ar has in this case the meanings listed above in Group 1.

Group 18

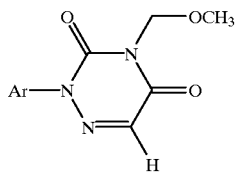
(IA-18)

Ar has in this case the meanings listed above in Group 1.

Group 19

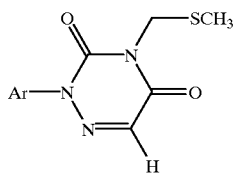
(IA-19)

Ar has in this case the meanings listed above in Group 1.

Group 20

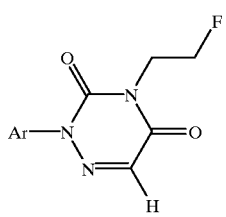
(IA-20)

Ar has in this case the meanings listed above in Group 1.

Group 21

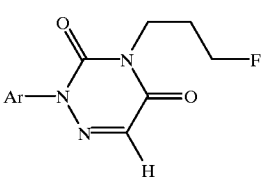
(IA-21)

Ar has in this case the meanings listed above in Group 1.

Group 22

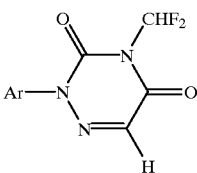
(IA-22)

Ar has in this case the meanings listed above in Group 1.

Group 23

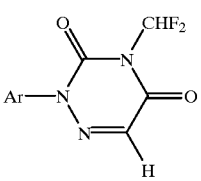
(IA-23)

Ar has in this case the meanings listed above in Group 1.

Group 24

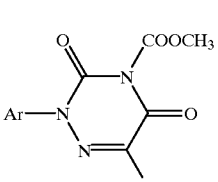
(IA-24)

Ar has in this case the meanings listed above in Group 1.

Group 25

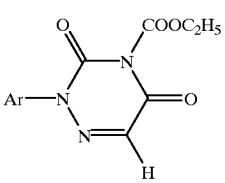
(IA-25)

Ar has in this case the meanings listed above in Group 1.

Group 26

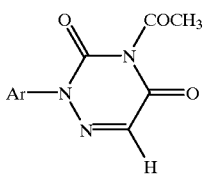
(IA-26)

Ar has in this case the meanings listed above in Group 1.

Group 27

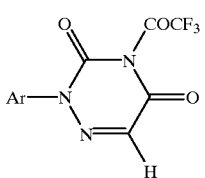
(IA-27)

Ar has in this case the meanings listed above in Group 1.

Group 28

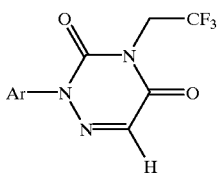
(IA-28)

Ar has in this case the meanings listed above in Group 1.

Group 29

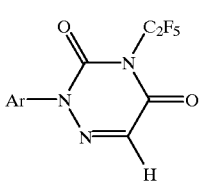
(IA-29)

Ar has in this case the meanings listed above in Group 1.

Group 30

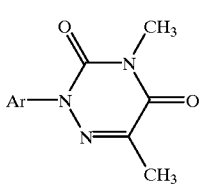
(IA-30)

Ar has in this case the meanings listed above in Group 1.

Group 31

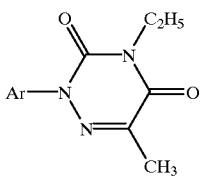
(IA-31)

Ar has in this case the meanings listed above in Group 1.

Group 32

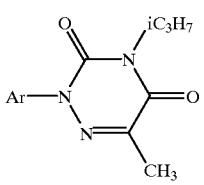
(IA-32)

Ar has in this case the meanings listed above in Group 1.

Group 33

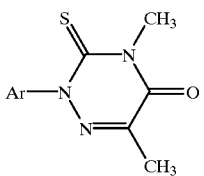
(IA-33)

Ar has in this case the meanings listed above in Group 1.

Group 34

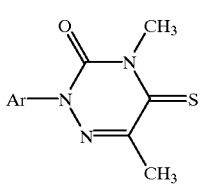
(IA-34)

Ar has in this case the meanings listed above in Group 1.

Group 35

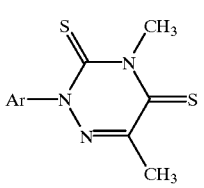
(IA-35)

Ar has in this case the meanings listed above in Group 1.
Group 36

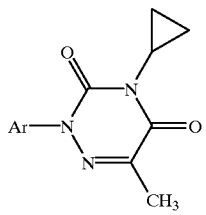
(IA-36)

Ar has in this case the meanings listed above in Group 1.
Group 37

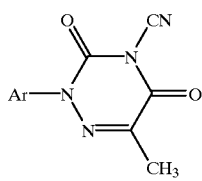
(IA-37)

Ar has in this case the meanings listed above in Group 1.
Group 38

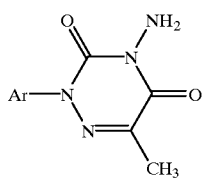
(IA-38)

Ar has in this case the meanings listed above in Group 1.
Group 39

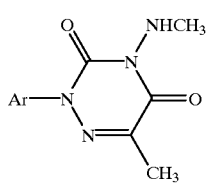
(IA-39)

Ar has in this case the meanings listed above in Group 1.
Group 40

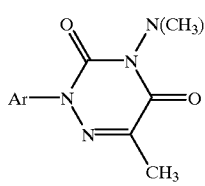
(IA-40)

Ar has in this case the meanings listed above in Group 1.
Group 41

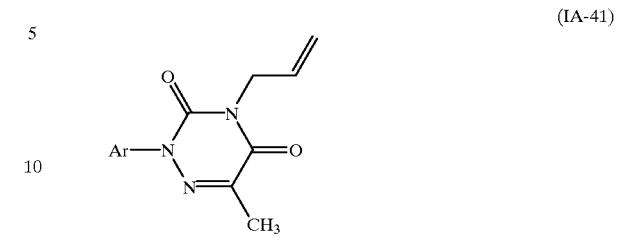
(IA-41)

Ar has in this case the meanings listed above in Group 1.
Group 42

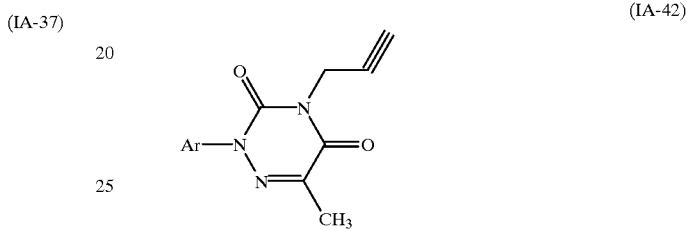
(IA-42)

Ar has in this case the meanings listed above in Group 1.
Group 43

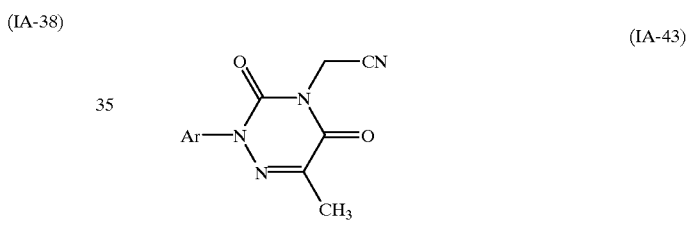
(IA-43)

Ar has in this case the meanings listed above in Group 1.
Group 44

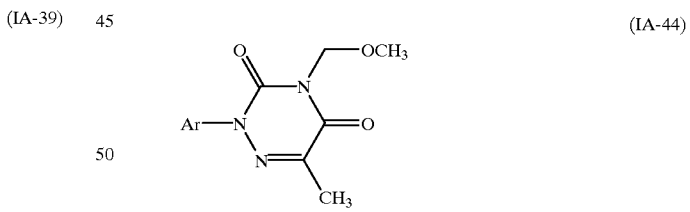
(IA-44)

Ar has in this case the meanings listed above in Group 1.
Group 45

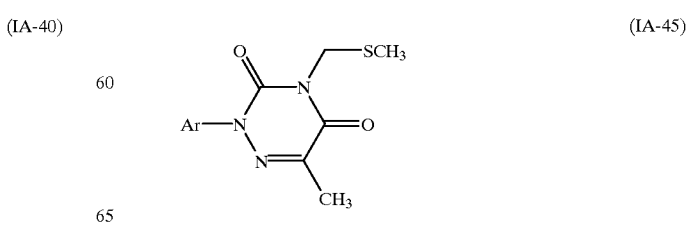
(IA-45)

Ar has in this case the meanings listed above in Group 1.
Group 46

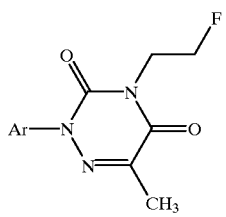
(IA-46)

Ar has in this case the meanings listed above in Group 1.
Group 47

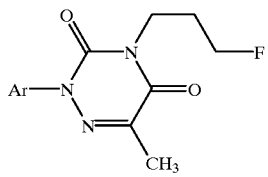
(IA-47)

Ar has in this case the meanings listed above in Group 1.
Group 48

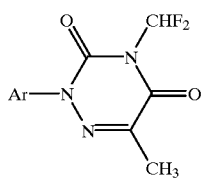
(IA-48)

Ar has in this case the meanings listed above in Group 1.
Group 49

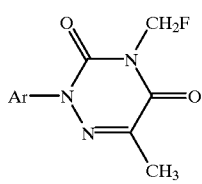
(IA-49)

Ar has in this case the meanings listed above in Group 1.
Group 50

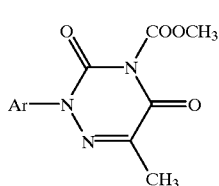
(IA-50)

Ar has in this case the meanings listed above in Group 1.
Group 51

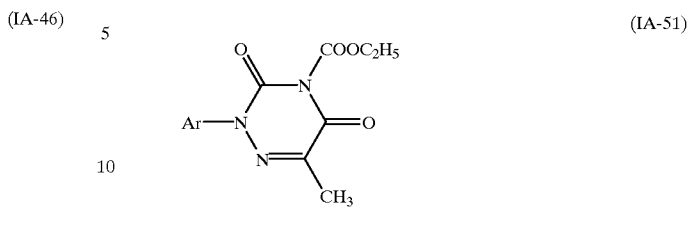
(IA-51)

Ar has in this case the meanings listed above in Group 1.
Group 52

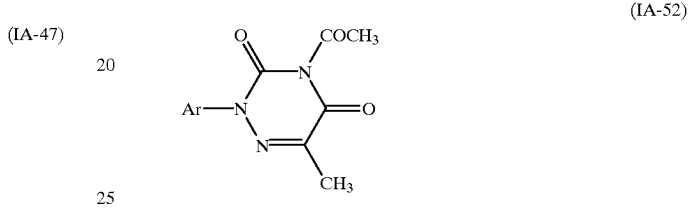
(IA-52)

Ar has in this case the meanings listed above in Group 1.
Group 53

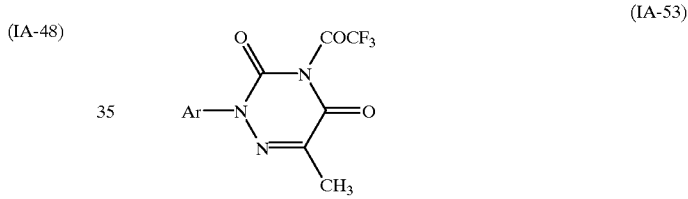
(IA-53)

Ar has in this case the meanings listed above in Group 1.
Group 54

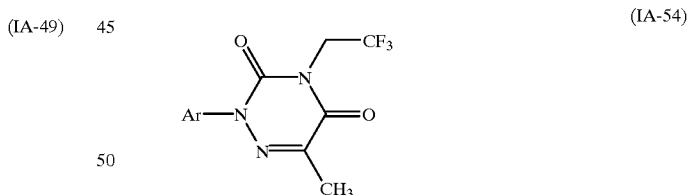
(IA-54)

Ar has in this case the meanings listed above in Group 1.
Group 55

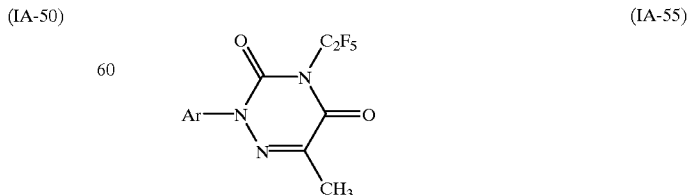
(IA-55)

Ar has in this case the meanings listed above in Group 1.
Group 56

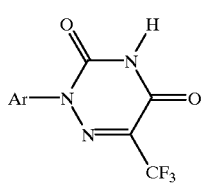

(IA-56)

Ar has in this case the meanings listed above in Group 1.
Group 57

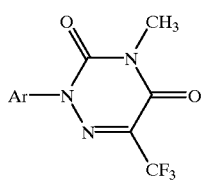

(IA-57)

Ar has in this case the meanings listed above in Group 1.
Group 58

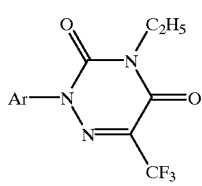

(IA-58)

Ar has in this case the meanings listed above in Group 1.
Group 59

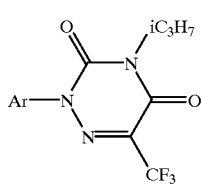

(IA-59)

Ar has in this case the meanings listed above in Group 1.
Group 60

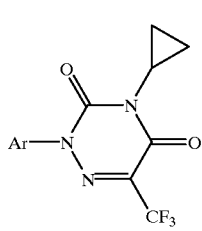

(IA-60)

Ar has in this case the meanings listed above in Group 1.
Group 61

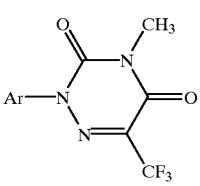

(IA-61)

Ar has in this case the meanings listed above in Group 1.
Group 62

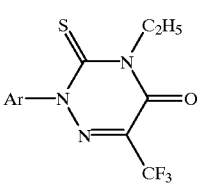

(IA-62)

Ar has in this case the meanings listed above in Group 1.
Group 63

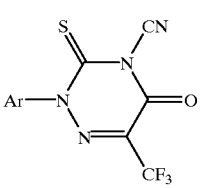

(IA-63)

Ar has in this case the meanings listed above in Group 1.
Group 64

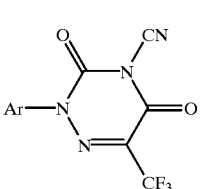

(IA-64)

Ar has in this case the meanings listed above in Group 1.
Group 65

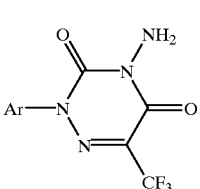

(IA-65)

Group 67

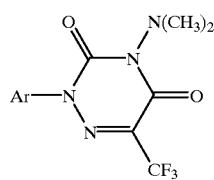
(IA-67)

Ar has in this case the meanings listed above in Group 1.
Group 68

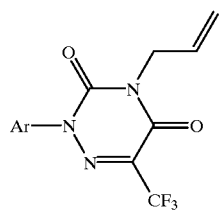
(IA-68)

Ar has in this case the meanings listed above in Group 1.
Group 69

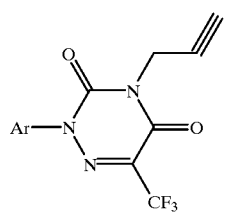
(IA-69)

Ar has in this case the meanings listed above in Group 1.
Group 70

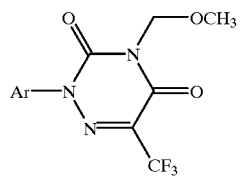
(IA-70)

Ar has in this case the meanings listed above in Group 1.
Group 71

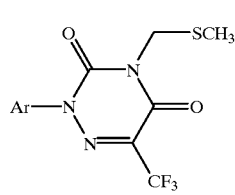
(IA-71)

Ar has in this case the meanings listed above in Group 1.
Group 72

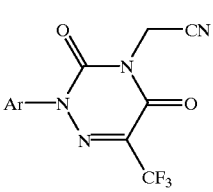
(IA-72)

Ar has in this case the meanings listed above in Group 1.
Group 73

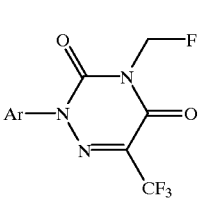
(IA-73)

Ar has in this case the meanings listed above in Group 1.
Group 74

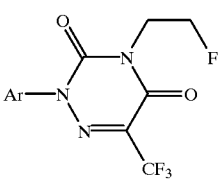
(IA-74)

Ar has in this case the meanings listed above in Group 1.
Group 75

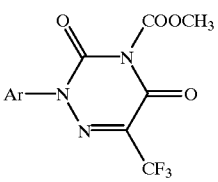
(IA-75)

Ar has in this case the meanings listed above in Group 1.
Group 76

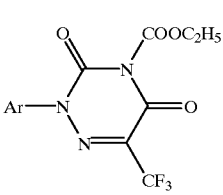
(IA-76)

Ar has in this case the meanings listed above in Group 1.

Group 77

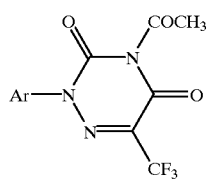
(IA-77)

Ar has in this case the meanings listed above in Group 1.

Group 78

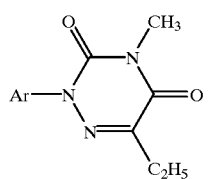
(IA-78)

Ar has in this case the meanings listed above in Group 1.

Group 79

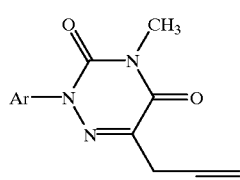
(IA-79)

Ar has in this case the meanings listed above in Group 1.

Group 80

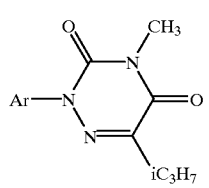
(IA-80)

Ar has in this case the meanings listed above in Group 1.

Group 81

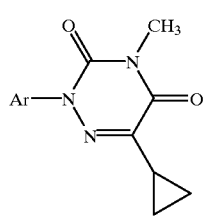
(IA-81)

Ar has in this case the meanings listed above in Group 1.

Group 82

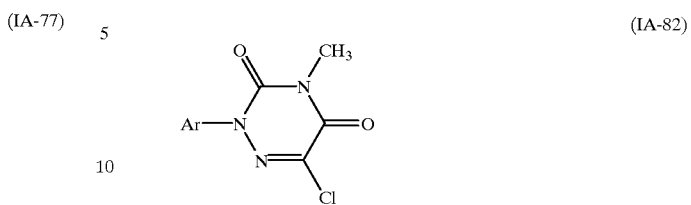
(IA-82)

Ar has in this case the meanings listed above in Group 1.

Group 83

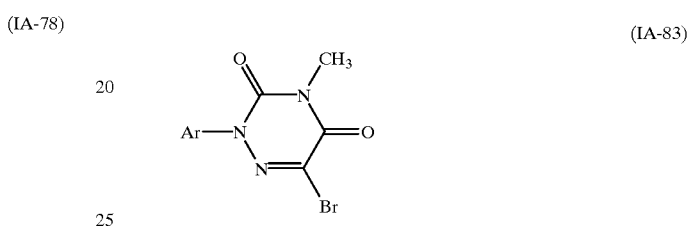
(IA-83)

Ar has in this case the meanings listed above in Group 1.

Group 84

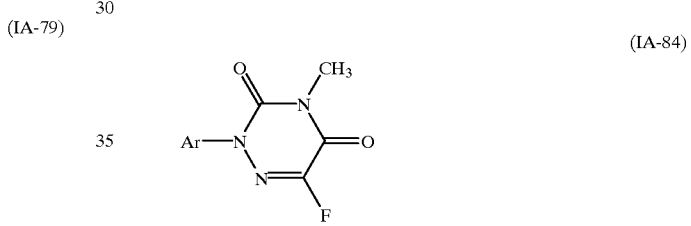
(IA-84)

Ar has in this case the meanings listed above in Group 1.

Group 85

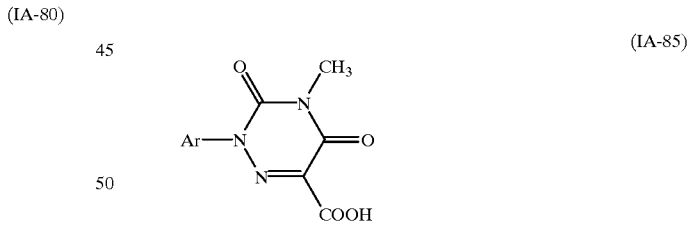
(IA-85)

Ar has in this case the meanings listed above in Group 1.

Group 86

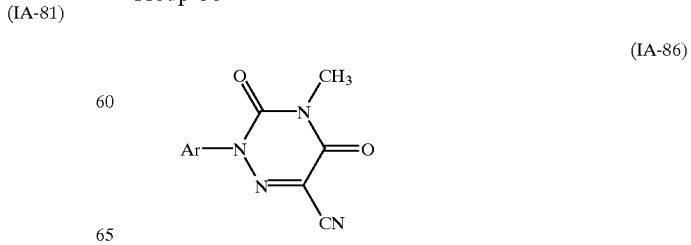
(IA-86)

Ar has in this case the meanings listed above in Group 1.
Group 87

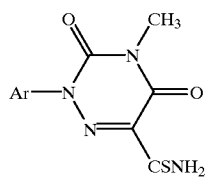
(IA-87)

Ar has in this case the meanings listed above in Group 1.
Group 88

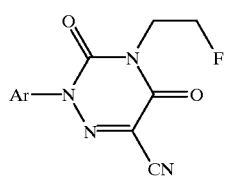
(IA-88)

Ar has in this case the meanings listed above in Group 1.
Group 89

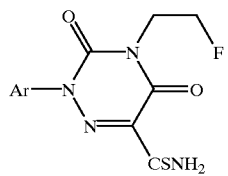
(IA-89)

Ar has in this case the meanings listed above in Group 1.
Group 90

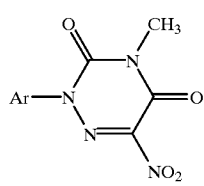
(IA-90)

Ar has in this case the meanings listed above in Group 1.
Group 91

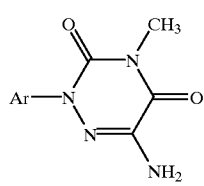
(IA-91)

Ar has in this case the meanings listed above in Group 1.
Group 92

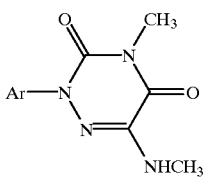
(IA-92)

Ar has in this case the meanings listed above in Group 1.
Group 93

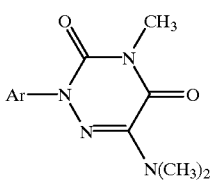
(IA-93)

Ar has in this case the meanings listed above in Group 1.
Group 94

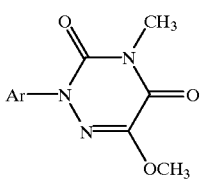
(IA-94)

Ar has in this case the meanings listed above in Group 1.
Group 95

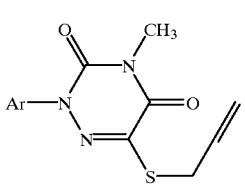
(IA-95)

Ar has in this case the meanings listed above in Group 1.
Group 96

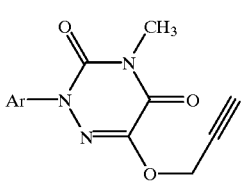
(IA-96)

Ar has in this case the meanings listed above in Group 1.

Group 97

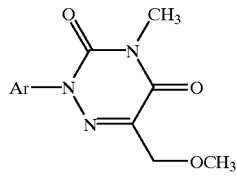

(IA-97)

Ar has in this case the meanings listed above in Group 1.

Group 98

(IA-98)

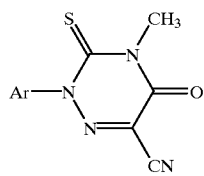

Ar has in this case the meanings listed above in Group 1.

Using, for example, 4,6-diethyl-1,2,4-triazine-3,5(2H, 4H)-dione and 2,4,5-trifluorobenzonitrile as starting materials, the course of the reaction in the process (a) according to the invention can be illustrated by the following equation:

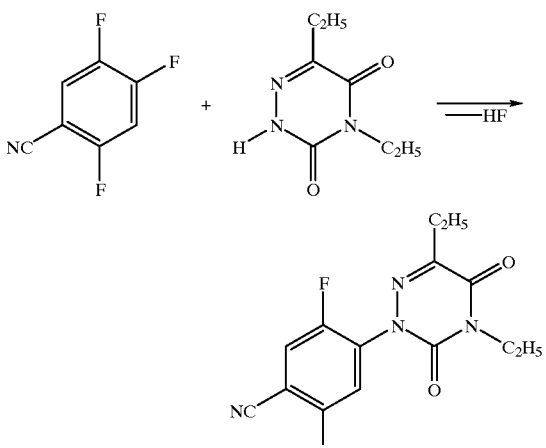

Using, for example, 2-(4-cyano-5-ethoxy-2-fluoro-phenyl)-6-trifluoromethyl-1,2,4-triazine-3,5(2H,4H)-dione and ethylbromide as starting materials, the course of the reaction in the process (b) according to the invention can be illustrated by the following equation:

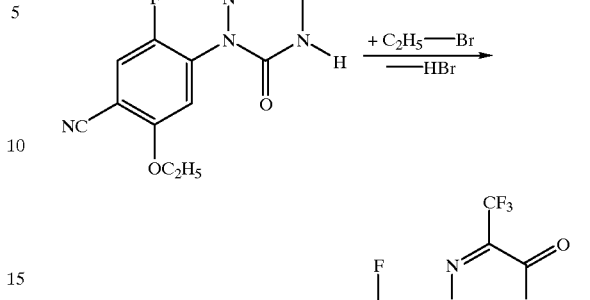

Using, for example, acetone N-(5-chloro-4-cyano-2-fluoro-phenyl)-hydrazone and potassium thiocyanate and, in the subsequent step, pyruvic acid as starting materials, the course of the reaction in the process (c) according to the invention can be illustrated by the following equation:

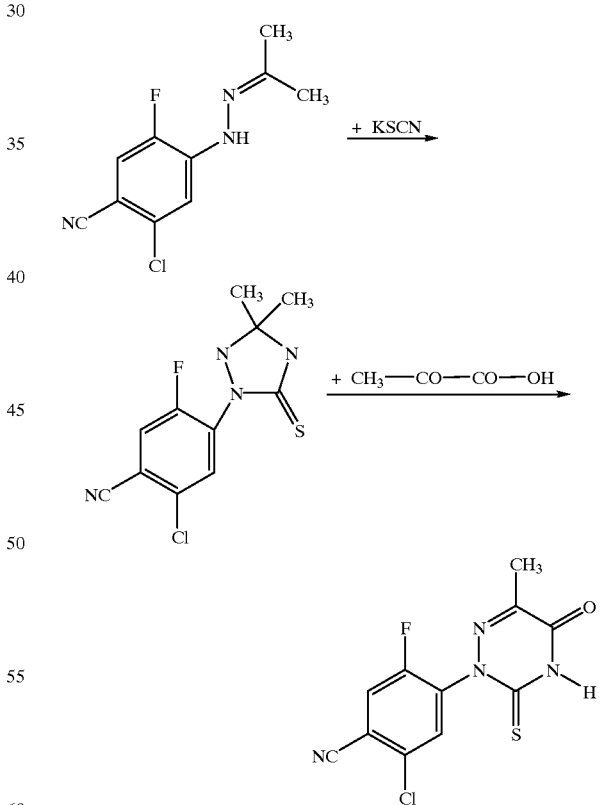

Using, for example, 4-amino-3-fluoro-2-methylthio-benzonitrile and ethyl cyano-acetylcarbamate as starting materials, the course of the reaction in the process (d) according to the invention can be illustrated by the following equation:

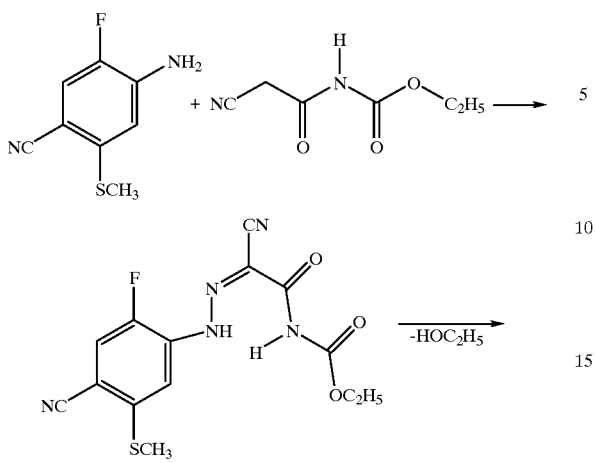

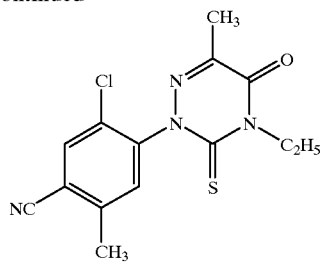

Using, for example, 4-amino-2,5-dichloro-benzonitrile and sodium nitrite/hydrochloric acid and, in the subsequent step, malonyldiethylurethane as starting materials, the course of the reaction in the process (f) according to the invention can be illustrated by the following equation:

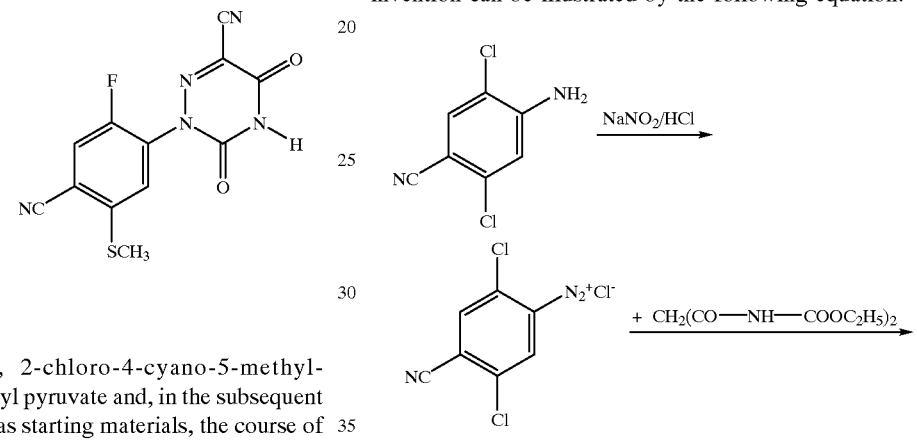

Using, for example, 2-chloro-4-cyano-5-methyl-phenylhydrazine and methyl pyruvate and, in the subsequent step, ethyl isothiocyanate as starting materials, the course of the reaction in the process (e) according to the invention can be illustrated by the following equation:

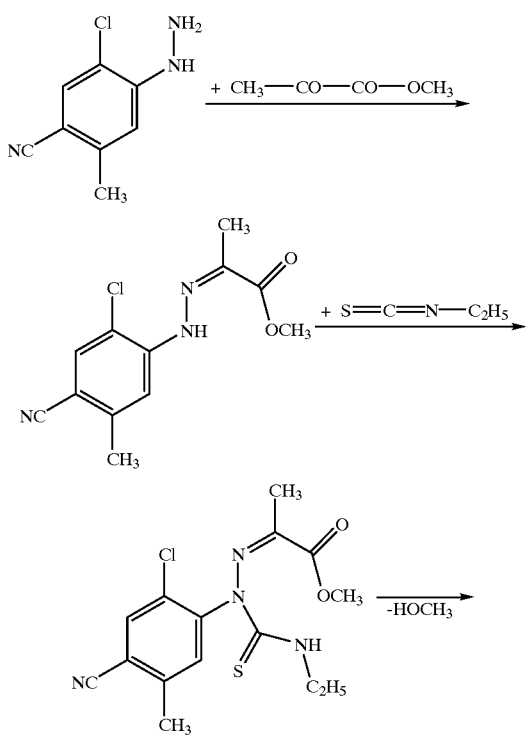

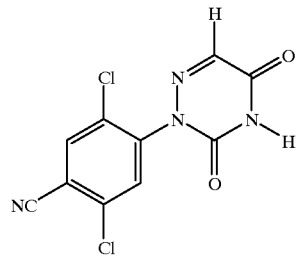

The formula (II) provides a general definition of the 1,2,4-triazine-3,5-di(thi)ones to be employed as starting materials in the process (a) according to the invention for preparing compounds of the formula (I). In the formula (II), $Q^1$, $Q^2$, $R^1$ and $R^2$ each preferably or in particular have those meanings which have already been indicated above, in connection with the description of the compounds of the formula (I) according to the invention, as being preferred or particularly preferred for $Q^1$, $Q^2$, $R^1$ and $R^2$.

The starting materials of the formula (II) are known and/or can be prepared by known methods (cf. J. Am. Chem. Soc. 80 (1958), 976; J. Heterocycl. Chem. 16 (1979), 1649; J. Org. Chem. 23 (1958), 1951–1953).

The formula (III) provides a general definition of the halogenobenzene derivatives furthermore to be used as starting materials in the process (a) according to the invention. In the formula (III), $R^3$, $R^4$ and $R^5$ each preferably or in particular have those meanings which have already been indicated above, in connection with the description of the compounds of the formula (I) according to the invention, as being preferred or particularly preferred for $R^3$, $R^4$ and $R^5$; $X^1$ preferably represents fluorine, chlorine or bromine, in particular fluorine.

The starting materials of the formula (III) are known and/or can be prepared by processes known per se (cf. EP 191181, EP 370332, EP 431373, EP 441004).

The formula (Ia) provides a general definition of the 2-aryl-1,2,4-triazine-3,5-di(thi)-ones to be employed as starting materials in the process (b) according to the invention. In the formula (Ia), $Q^1$, $Q^2$, $R^2$, $R^3$, $R^4$ and $R^5$ each preferably or in particular have those meanings which have already been indicated above, in connection with the description of the compounds of the formula (I) according to the invention, as being preferred or particularly preferred for $Q^1$, $Q^2$, $R^2$, $R^3$, $R^4$ and $R^5$.

The starting materials of the formula (Ia) are novel compounds according to the invention; they can be prepared by the processes (a) and (c) to (f) according to the invention.

The formula (IV) provides a general definition of the alkylating agents furthermore to be employed as starting materials in the process (b) according to the invention. In the formula (IV), $R^1$ preferably or in particular has those meanings which have already been indicated above, in connection with the description of the compounds of the formula (I) according to the invention, as being preferred or particularly preferred for $R^1$; $X^2$ preferably represents fluorine, chlorine, bromine, iodine, methoxysulphonyloxy or ethoxysulphonyloxy, in particular chlorine or bromine.

The starting materials of the formula (IV) are known organic chemicals for synthesis.

The formula (V) provides a general definition of the arylhydrazones to be employed as starting materials in the process (c) according to the invention for preparing compounds of the formula (I). In the formula (V), $R^3$, $R^4$ and $R^5$ each preferably or in particular have those meanings which have already been indicated above, in connection with the description of the compounds of the formula (I) according to the invention, as being preferred or particularly preferred for $R^3$, $R^4$ and $R^5$.

The starting materials of the formula (V) are known and/or can be prepared by known processes (cf. WO 86/00072, U.S. Pat. No. 4,956,004).

The formula (VI) provides a general definition of the alkali metal (thio)cyanates furthermore to be employed as starting materials in the process (c) according to the invention. In the formula (VI), $Q^1$ preferably or in particular has those meanings which have already been indicated above, in connection with the description of the compounds of the formula (I) according to the invention, as being preferred or particularly preferred for $Q^1$; M preferably represents lithium, sodium, potassium, rubidium or caesium, in particular sodium or potassium.

The starting materials of the formula (VI) are known chemicals for synthesis.

The formula (VIII) provides a general definition of the ketocarboxylic acids furthermore to be employed as starting materials in the process (c) according to the invention. In the formula (VIII), $R^2$ preferably or in particular has those meanings which have already been indicated above, in connection with the description of the compounds of the formula (I) according to the invention, as being preferred or particularly preferred for $R^2$.

The starting materials of the formula (VIII) are known organic chemicals for synthesis.

The formula (IX) provides a general definition of the aryl amines to be employed as starting materials in the processes (d) and (f) according to the invention for preparing compounds of the formula (I). In the formula (IX), $R^3$, $R^4$ and $R^5$ each preferably or in particular have those meanings which have been indicated above, in connection with the description of the compounds of the formula (I) according to the invention, as being preferred or particularly preferred for $R^3$, $R^4$ and $R^5$.

The starting materials of the formula (IX) are known and/or can be prepared by known processes (cf. EP 224001, EP 303573, DE 3835168, EP 403891).

The formula (X) provides a general definition of the cyanoacetylcarbamic acid esters furthermore to be employed as starting materials in the process (d) according to the invention. In the formula (X), $R^1$ preferably or in particular has those meanings which have already been indicated above, in connection with the description of the compounds of the formula (I) according to the invention, as being preferred or particularly preferred for $R^1$.

The starting materials of the formula (X) are known organic chemicals for synthesis.

The formula (XII) provides a general definition of the arylhydrazines to be employed as starting materials in the process (e) according to the invention for preparing compounds of the formula (I). In the formula (XII), $R^3$, $R^4$ and $R^5$ each preferably or in particular have those meanings which have already been indicated above, in connection with the description of the formula (I) according to the invention, as being preferred or particularly preferred for $R^3$, $R^4$ und $R^5$.

The starting materials of the formula (XII) are known and/or can be prepared by known processes (cf. EP 370332).

The formula (XIII) provides a general definition of the ketocarboxylic acid derivatives furthermore to be employed as starting materials in the process (e) according to the invention. In the formula (XIII), $R^2$ preferably or in particular has those meanings which have already been indicated above, in connection with the description of the is compounds of the formula (I) according to the invention, as being preferred or particularly preferred for $R^2$; R preferably represents hydrogen or $C_1$–$C_4$-alkyl, in particular hydrogen, methyl or ethyl.

The starting materials of the formula (XIII) are known organic chemicals for synthesis.

The formula (XV) provides a general definition of the iso(thio)cyanates furthermore to be employed as starting materials in the process (e) according to the invention. In the formula (XV), $Q^1$ and $R^1$ preferably or in particular have those meanings which have already been indicated above, in connection with the description of the compounds of the formula (I) according to the invention, as being preferred or particularly preferred for $Q^1$ and $R^1$.

The starting materials of the formula (XV) are known chemicals for synthesis.

The malonyldiurethane of the formula (XVII) to be employed as starting material in the process according to the invention is a known chemical for synthesis.

Suitable diluents for carrying out the processes (a) to (f) according to the invention are in particular inert organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

Suitable reaction auxiliaries for the processes (a) to (f) are generally the customary inorganic or organic bases or acid accepters. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, or i-, s- or t-butoxide or potassium n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-di-methyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2 -methyl-pyridine, 4-dimethylamino-pyridine, N-methyl-piperidine, 1,4-diazabicyclo-[2,2,2]-octane (DABCO), 1,5-diazabicyclo[4,3,0]-non-5-ene (DBN), or 1,8-diazabicyclo[5,4,0]-undec-7-ene (DBU).

When carrying out the processes (a) to (f) according to the invention, the reaction temperatures can be varied within a relatively wide range. In general, temperatures of between −20° C. and +150° C., preferably between 0° C. and +120° C., are employed.

The processes (a) to (f) according to the invention are generally carried out under atmospheric pressure. However, it is also possible to carry out the processes according to the invention under elevated or reduced pressure—in general beween 0,1 bar and 10 bar.

In the practice of the processes (a) to (f) according to the invention, the starting materials are generally employed in approximately equimolar amounts. However, it is also possible to use in each case one of the components in a relatively large exess. The reaction is generally carried out in a suitable diluent in the presence of a reaction auxiliary, and the reaction mixture is generally stirred for a number of hours at the temperature required. Work-up is carried out by customary methods (cf. the Preparation Examples).

The active compounds according to the invention can be used as defoliants, desiccants, haulm killers and, especially as weed killers. By weeds in the broadest sense, there are to be understood all plants which grow in locations where they are undesirable. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita. Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostic, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual cultures.

The compounds of the formula (I) according to the invention are suitable in particular for selectively controlling monocotyledonous and dicotyledonous weeds in monocotyledonous and docotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumise, sepiolite and dolomite, as well as synthetic granules of inorganic and organic meals, and granules of organic material such as sawdust, coconut shells, maize cobs and tobacco stalks; suitable emulsifiers and/or foam-forming agents are: for example nonionic and anionic emulsifers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonylureas, such as amidosulfuiron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; and others, such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing. The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the Examples below.

PREPARATION EXAMPLES

Example 1

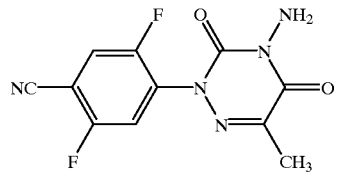

At 70° C., 7.1 g (50 mMol) of 4-amino-6-methyl-1,2,4-triazine-3,5(2H,4H)-dione, 6.9 g (50 mMol) of potassium carbonate and 7.9 g (50 mMol) of 2,4,5-Trifluoro-benzonitrile in 100 ml of dimethyl sulphoxide are stirred for 4 hours, the mixture is subsequently cooled to room temperature and stirred into ice-water and precipitated product is filtered off with suction, dried and recrystallized from ethanol.

2.9 g (20% of theory) of 2-(2,4-difluoro-4-cyano-phenyl)-4-amino-4-methyl-1,2,4-triazine-3,5(2H,4H)-dione of melting point 125° C. are obtained.

Example 2

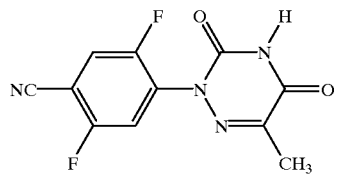

At 120° C., 2.54 g (20 mMol) of 6-methyl-1,2,4-triazine-3,5(2H,4H)-dione in 50 ml of dimethyl sulphoxide are stirred with 2.8 g (20 mMol) of potassium carbonate and 3.14 g (20 mol) of 2,4,5-trifluoro-benzonitrile for 12 hours, the mixture is subsequently cooled to room temperature and stirred with water, the pH is adjusted to using hydrochloric acid and precipitated product is filtered off with suction, stirred with water and dried.

4.6 g (87% of theory) of 2-(2,4-difluoro-4-cyano-phenyl)-6-methyl-1,2,4-triazine-3,5(2H,4H)-dione of melting point 214° C. are obtained.

Example 3

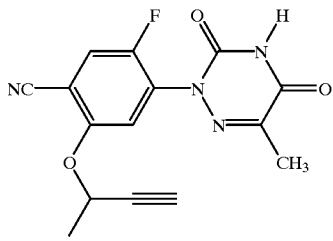

5.2 g (20 mMol) of 2-(2,4-difluoro-4-cyano-phenyl)-6-methyl-1,2,4-triazine-3,5(2H,4H)-dione are initially charged in 50 ml of acetonitrile with 2.8 g (40 mMol) of 3-butin-2-ol, and at room tempeature (about 20° C.), the mixture is mixed a little at a time with 1.15 g (40 mMol) of sodium hydride (80% strength in paraffin) and the mixture is stirred at room temperature for 12 hours. The mixture is concentrated under reduced pressure, the residue is stirred with water, the pH is adjusted to 5 using concentrated hydrochloric acid and the precipitated product is isolated by filtration.

5.8 g (92% of theory) of 2-(2-fluoro-4-cyano-5-but-1-in-3-yl-oxy-phenyl)-6-methyl-1,2,4-triazine-3,5(2H,4H)-dione of melting point 153° C. (decomp.) are obtained.

Example 4

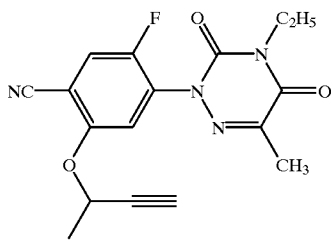

At room temperature (about 20° C.), 1.6 g (5 mMol) of 2-(2-fluoro-4-cyano-5-but-1-in-3-yl-oxy-phenyl)-6-methyl-1,2,4-triazine-3,5(2H,4H)-dione in 50 ml of dimethyl sulphoxide are stirred with 1.38 g (10 mMol) of potassium carbonate and 1.56 g (10 mMol) of ethyl iodide for 12 hours. The mixture is concentrated under reduced pressure, the residue is stirred with water, the pH is adjusted to 5 using concentrated hydrochloric acid and the precipitated product is isolated by filtration.

1.6 g (93.5% of theory) of 2-(2-fluoro-4-cyano-5-but-1-in-3-yl-oxy-phenyl)-4-ethyl-6-methyl-1,2,4-triazine-3,5(2H,4H)-dione of melting point 139° C. are obtained.

Similar to Preparation Examples 1 to 4 and in accordance with the general description of the preparation processes according to the invention, it is also possible, for example, to prepare the compounds of the formula (I) listed in Table 1 below.

(I)

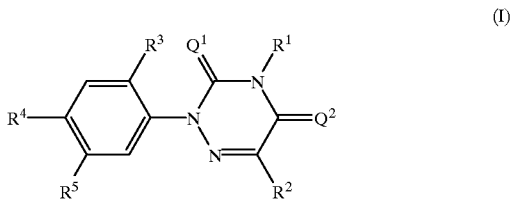

TABLE 1

Examples of compounds of the general formula (I)

| Ex. No. | $R^1$ | $R^2$ | $Q^1$ | $Q^2$ | $R^3$ | $R^4$ | $R^5$ | Physical Data |
|---|---|---|---|---|---|---|---|---|
| 5 | $NH_2$ | $C(CH_3)_3$ | O | O | F | CN | F | Mp.: 120° C. |
| 6 | H | H | O | O | F | CN | F | Mp.: >250° C. |
| 7 | H | $CH_3$ | O | O | F | CN | F | Mp.: 130° C. |
| 8 | $CH_3$ | $CH_3$ | O | O | F | CN | $OCH(CH_3)C\equiv CH$ | Mp.: 102° C. |
| 9 | H | H | O | O | F | CN | $OCH(CH_3)C\equiv CH$ | Mp.: 202° C. |
| 10 | $CH_3$ | H | O | O | F | CN | $OCH(CH_3)C\equiv CH$ | Mp.: 129° C. |
| 11 | H | H | O | O | F | CN | $NHSO_2C_2H_5$ | Mp.: 121° C. (Decomp.) |
| 12 | H | H | O | O | F | CN | $OCH_2-C\equiv CH$ | Mp.: 175° C. |
| 13 | $CH_3$ | H | O | O | F | CN | $OCH_2-C\equiv CH$ | Mp.: 137° C. |
| 14 | $CH_3$ | H | O | O | F | CN | $NHSO_2C_2H_5$ [contains about 30% $-N(CH_3)-$] | Mp.: 187° C. |
| 15 | $CH_3$ | H | O | O | F | CN | $OCH_2CH=CH_2$ | Mp.: 139° C. |
| 16 | $CH(CH_3)_2$ | $CH_3$ | O | O | F | CN | $OCH(CH_3)C\equiv CH$ | Mp.: 112° C. |
| 17 | $C_2H_5$ | H | O | O | F | CN | $OC_2H_5$ | Mp.: 142° C. |
| 18 | $C_2H_5$ | H | O | O | F | CN | $OCH_2-C\equiv CH$ | $^1$H NMR: |
| 19 | $C_2H_5$ | H | O | O | F | CN | $OCH(CH_3)C\equiv CH$ | Mp.: 132° C. |
| 20 | $CH(CH_3)_2$ | H | O | O | F | CN | $OCH(CH_3)C\equiv CH$ | Mp.: 70° C. |
| 21 | H | H | O | O | F | CN | $OC_2H_5$ | Mp.: 150° C. |
| 22 | H | H | O | O | F | CN | OH | Mp.: 220° C. |
| 23 | $CH_2CH_2F$ | H | O | O | F | CN | $OCH(CH_3)C\equiv CH$ | |
| 24 | $(CH_2)_3F$ | H | O | O | F | CN | $OCH(CH_3)C\equiv CH$ | |
| 25 | $CH_2-C\equiv CH$ | H | O | O | F | CN | $OCH(CH_3)C\equiv CH$ | Mp.: 132° C. |
| 26 | $CH_2CH_2F$ | $CH_3$ | O | O | F | CN | $OCH(CH_3)C\equiv CH$ | Mp.: 119° C. |

TABLE 1-continued

Examples of compounds of the general formula (I)

| Ex. No. | $R^1$ | $R^2$ | $Q^1$ | $Q^2$ | $R^3$ | $R^4$ | $R^5$ | Physical Data |
|---|---|---|---|---|---|---|---|---|
| 27 | $(CH_2)_3F$ | $CH_3$ | O | O | F | CN | $OCH(CH_3)C\equiv CH$ | Mp.: 115° C. |
| 28 | $CH_3$ | $CH_3$ | O | O | F | CN | $NHSO_2C_2H_5$ | Mp.: 129° C. |
| 29 | $CH_2CH=CH_2$ | H | O | O | F | CN | $OCH(CH_3)C\equiv CH$ | Mp.: 84° C. |
| 30 | $CH_3$ | $CH_3$ | O | O | F | CN | $NHSO_2CH_3$ | Mp.: 115° C. |
| 31 | $(CH_2)_3F$ | H | O | O | F | CN | F | Mp.: 85° C. |
| 32 | H | $CH_3$ | O | O | F | CN | $NHSO_2CH_3$ | Mp.: 140° C. |
| 33 | $(CH_2)_3F$ | $CH_3$ | O | O | F | CN | $NHSO_2CH_3$ | Mp.: 108° C. |
| 34 | $CH_3$ | H | O | S | F | CN | $OCH(CH_3)C\equiv CH$ | (amorphous) |
| 35 | $CH_2CH_2F$ | H | O | O | F | CN | $OCH_2C\equiv CH$ | Mp.: 135° C. |
| 36 | $(CH_2)_2CF=CF_2$ | H | O | O | F | CN | $OCH_2C\equiv CH$ | (amorphous) |
| 37 | $(CH_2)_3F$ | H | O | O | F | CN | $OCH_2C\equiv CH$ | Mp.: 126° C. |
| 38 | $(CH_2)_2CF=CF_2$ | H | O | O | F | CN | $NHSO_2C_2H_5$ | Mp.: 88° C. |
| 39 | $(CH_2)_3F$ | $CH_3$ | O | O | F | $CSNH_2$ | $NHSO_2CH_3$ | Mp.: >210° C. |
| 40 | $C_2H_5$ | H | O | O | F | CN | $N(C_2H_5)SO_2C_2H_5$ | Mp.: 154° C. |
| 41 | $CH_3$ | H | O | O | F | CN | $N(CH_3)SO_2C_2H_5$ | Mp.: 91° C. |
| 42 | H | H | O | O | F | CN | $N(SO_2C_2H_5)_2$ | Mp.: >250° C. |
| 43 | $CH_3$ | H | O | O | F | CN | $N(SO_2C_2H_5)_2$ | Mp.: 164° C. |
| 44 | $CH_3$ | H | O | O | F | CN | $NHSO_2C_2H_5$ | Mp.: 233° C. |
| 45 | $CH_2CH_2F$ | H | O | O | F | CN | $NHSO_2C_2H_5$ | Mp.: 190° C. |
| 46 | $(CH_2)_3F$ | H | O | O | F | CN | $NHSO_2C_2H_5$ | Mp.: 98° C. |
| 47 | $(CH_2)_3F$ | H | O | O | F | CN | $NHSO_2CH_3$ | Mp.: 186° C. |
| 48 | $CH_2CH_2F$ | H | O | O | F | CN | $NHSO_2CH_3$ | Mp.: 178° C. |

USE EXAMPLES

Example A

Pre-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of the active compound. Advantageously, the amount of water per unit area is kept constant. The active compound concentration in the preparation is not important, only the active compound application rate per unit area matters.

After three weeks, the degree of damage to the plants is rated in % damage in comparison with the development of the untreated control.

The figures denote:

0%=no effect (like untreated control)

100%=total destruction

In this test, for example, the compounds of Preparation Example 7, 8, 10, 17, 18 and 19 exhibit, at an application rate between 60 and 125 g/ha, very strong activity against weeds such as Alopecurus (70 to 100%), Digitaria (70 to 100%), Sorghum (70 to 100%), Amaranthus (100%), Chenopodium (100%) and Solanum (100%), and they are tolerated well by crops, such as, for example, wheat (up to 20%), barley (0 to 10%), Maize (0%), Soya (10 to 20%) and cotton (0 to 30%)

Example B

Post-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15cm are sprayed with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 7, 8 and 10 exhibit, at outwall rates between 60 and 125 g/ha, very strong activity against weeds such as Digitaria (70 to 95%), Echinochloa (80 to 100%), Setaria (70 to 100%), Datura (100%), Solanum (100%) and Viola (100%), and they are well tolerated by crops, such as, for example, wheat (0 to 10%) and barley (0%).

What is claimed is:
1. Substituted 2-aryl-1,2,4-triazine-3,5-di(thi)ones of the formula (I):

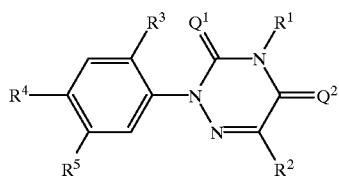

$Q^1$ represents oxygen or sulphur,
$Q^2$ represents oxygen or sulphur,
$R^1$ represents cyano, amino, represents respectively optionally cyano-fluorine-, chlorine-, $C_1$–$C_4$-alkoxy- or $C_1$–$C_4$-alkylthio-substituted alkyl, alkoxy, alkylamino, dialkylamino, alkylcarbonyl or alkoxycarbonyl having in each case 1 to 6 carbon atoms in the alkyl groups, represents respectively optionally fluorine-, chlorine- or bromine-substituted alkenyl, alkenylcarbonyl, alkenyloxycarbonyl, alkinyl, alkinylcarbonyl or alkinyloxycarbonyl having in each case 2 to 6 carbon atoms in the alkenyl or alkinyl groups, or represents respectively optionally cyano-, fluorine-, chlorine-, bromine- or $C_1$–$C_4$-alkyl-substituted cycloalkyl or cycloalkylalkyl having in each case 3 to 6 carbon atoms in the cycloalkyl groups and optionally 1 to 4 carbon atoms in the alkyl moiety,
$R^2$ represents hydrogen, halogen, nitro, carboxyl, cyano, thiocarbamoyl, amino, represents respectively optionally cyano-, fluorine-, chlorine-, $C_1$–$C_4$-alkoxy- or $C_1$–$C_4$-alkylthio-substituted alkyl, alkoxy, alkylthio, alkylamino or dialkylamino having in each case 1 to 6 carbon atoms in the alkyl groups, represents respectively optionally fluorine-, chlorine- or bromine-substituted alkenyl, alkenyloxy, alkenylthio, alkinyl, alkinyloxy or alkinylthio having in each case 2 to 6 carbon atoms in the alkenyl- or alkinyl-groups, or represents respectively optionally cyano-, fluorine-, chlorine-, bromine- or $C_1$–$C_4$-alkyl-substituted cycloalkyl or cycloalkylalkyl having in each case 3 to 6 carbon atoms in the cycloalkyl groups and optionally 1 to 6 carbon atoms in the alkyl moiety,
$R^3$ represents fluorine, chlorine or bromine,
$R^4$ represents cyano or thiocarbamoyl and
$R^5$ represents the grouping —$A^1$—$A^2$—$A^3$,
in which
$A^1$ represents a single bond, represents oxygen, sulphur, —SO—, —$SO_2$—, —CO— or the grouping —N—$A^4$—, where $A^4$ represents hydrogen, hydroxyl, $C_1$–$C_4$-alkyl, $C_3$–$C_4$-alkenyl, $C_3$–$C_4$-alkinyl, $C_1$–$C_4$-alkoxy, phenyl, $C_1$–$C_4$-alkylsulphonyl or phenylsulphonyl,
$A^1$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene,
$A^2$ represents a single bond, represents oxygen, sulphur, —SO—, —$SO_2$—, —CO— or the grouping —N—$A^4$—, where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl,
$A^2$ furthermore represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene,
$A^3$ represents hydrogen, with the proviso that in this case $A^1$ and/or $A^2$ do not represent a single bond,
$A^3$ furthermore represents hydroxyl, amino, cyano, isocyano, thiocyanato, nitro, carboxyl, carbamoyl, thiocarbamoyl, sulpho, chlorosulphonyl, fluorine, chlorine, bromine, represents respectively optionally fluorine-, chlorine- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy-(thio)phosphoryl having in each case 1 to 6 carbon atoms in the alkyl groups, represents respectively optionally fluorine- or chlorine-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, represents respectively optionally fluorine-, chlorine-, cyano-, carboxyl-, $C_1$–$C_4$-alkyl- and/or $C_1$–$C_4$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, or represents respectively optionally nitro-cyano-, carboxyl-, fluorine-, chlorine-, bromine-, $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxy-carbonyl-substituted phenyl, phenyloxy, phenyl-$C_1$–$C_4$-alkyl, phenyl-$C_1$–$C_4$-alkoxy, phenyloxycarbonyl orphenyl-$C_1$–$C_4$-alkoxycarbonyl,
$A^3$ furthermore represents respectively optionally fully or partially hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazol-$C_1$–$C_4$-alkyl, pyridinyl-$C_1$–$C_4$-alkyl, pyrimidinyl-$C_1$–$C_4$-alkyl, pyrazolylmethoxy, furylmethoxy, represents perhydropyranylmethoxy or pyridylmethoxy,
except for those compounds wherein:
a) $A^1$ and $A^2$ in formula (I) are the same and both stand for a group selected from S, O, —SO— and —$SO_2$—;
b) $A^1$ and $A^2$ both represent —CO— and $A^3$ represents hydrogen; and
c) $A^1$ and $A^2$ both represent a single bond and $A^3$ represents pyrrolyl, pyrazolyl, imidazolyl, triazolyl, furyl, oxiranyl, oxetanyl, dioxolanyl, thienyl, oxazolyl, isooxazolyl, thiazolyl, isothiazolyl, oxadiazolyl, thiadiazolyl, pyridinyl, pyrimidinyl or triazinyl.
2. Substituted 2-aryl-1,2,4-triazine-3,5-di(thi)ones of the formula (I) according to claim 1,
wherein
$Q^1$ represents oxygen or sulphur,
$Q^2$ represents oxygen or sulphur,
$R^1$ represents cyano, amino, represents respectively optionally cyano-, fluorine-, chlorine-, methoxy- or ethoxy-substituted methyl, ethyl, n- or i-propyl, n-, i- s- or t-butyl, methoxy, ethoxy, n- or i-propoxy, n-, i-, s- or t-butoxy, methylamino, ethylamino, n- or i-propylamino, n-, i-, s- or t-butylamino, dimethylamino, diethylamino, acetyl, propionyl, n- or i-butyroyl, methoxycarbonyl, ethoxycarbonyl, n- or i-propoxycarbonyl, represents respectively optionally fluorine-, chlorine- or bromine-substituted propenyl, butenyl, propenylcarbonyl, butenylcarbonyl, propenyloxycarbonyl, butenyloxycarbonyl, represents propinyl, butinyl, propinylcarbonyl, butinylcarbonyl, propinyloxy-carbonyl or butinyloxycarbonyl, or represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, $R^2$ represents hydrogen, halogen, nitro, carboxyl, cyano, thiocarbamoyl, amino, represents respectively optionally cyano-, fluorine-, chlorine-, methoxy- or ethoxy-substituted methyl, ethyl, n- or i-propyl, n-, i- s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, represents respectively optionally fluorine-, chlorine- or bromine-substituted propenyl, propenyloxy, propenylthio, butenyl, butenyloxy or butenylthio, represents propinyl, propinyloxy, propinylthio, butinyl, butinyloxy or butinylthio, or represents respectively optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, $R^3$ represents fluorine or chlorine, $R^4$ represents cyano or thiocarbamoyl, and $R^5$ represents the grouping —$A^1$—$A^2$—$A^3$,
 in which
  $A^1$ represents a single bond, represents oxygen, sulphur, —SO—, —SO$_2$—, —CO— or the grouping —N—$A^4$—, where $A^4$ represents hydrogen, hydroxyl, methyl, ethyl, n- or i-propyl, methoxy, ethoxy, n- or i-propoxy, methylsulphonyl or ethylsulphonyl,
  $A^1$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl,
  $A^2$ represents a single bond, represents oxygen, sulphur, —SO—, —SO$_2$—, —CO— or the grouping —N—$A^4$—, where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl,
  $A^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl or propine-1,3-diyl,
  $A^3$ represents hydrogen, with the proviso that in this case $A^1$ and/or $A^2$ do not represent a single bond,
  $A^3$ furthermore represents hydroxyl, amino, cyano, nitro, carboxyl, carbamoyl, sulpho, fluorine, chlorine, bromine, represents respectively optionally fluorine-, chlorine-, methoxy- or ethoxy-substituted methyl, ethyl, n- or i-propyl, n-, i-, s- or t-butyl, n- i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphinyl, ethyl-sulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl or dipropoxyphosphoryl, diisopropoxyphosphoryl, represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, represents respectively optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexyloxycarbonyl, cyclopentylmethoxycarbonyl or cyclohexylmethoxycarbonyl, or represents respectively optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl,
  $A^3$ furthermore represents (in each case optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy.

except for those compounds wherein:
  a) $A^1$ and $A^2$ in formula (I) are the same and both stand for a group selected from S, O, —SO— and —SO$_2$—;
  b) $A^1$ and $A^2$ both represent —CO— and $A^3$ represents hydrogen; and
  c) $A^1$ and $A^2$ both represent a single bond and $A^3$ represents pyrrolyl, pyrazolyl, imidazolyl, triazolyl, furyl, oxiranyl, oxetanyl, dioxolanyl, thienyl, oxazolyl, isooxazolyl, thiazolyl, isothiazolyl, oxadiazolyl, thiadiazolyl, pyridinyl, pyrimidinyl or triazinyl.

3. A process for preparing substituted 2-aryl-1,2,4-triazine-3,5-di(thi)one of the formula (I),

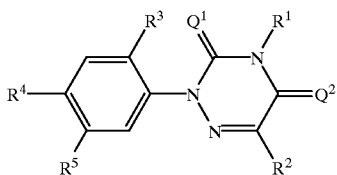 (I)

in which
$R^1, R^2, R^3, R^4, R^5, Q^1$, and $Q^2$ are each as defined in claim 1
wherein
(a) 1,2,4-triazine-3,5-di(thi)ones of the formula (II),

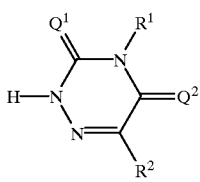 (II)

in which
$Q^1, Q^2, R^1$ and $R^2$ are each as defined above,
are reacted with halogenobenzene derivatives of the formula (III),

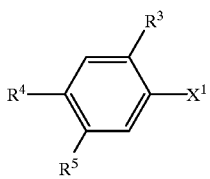 (III)

in which
$R^3, R^4$ and $R^5$ are each as defined above and
$X^1$ represents halogen,
optionally in the presence of a diluent and optionally in the presence of a reaction auxiliary,
or that
(b) 2-aryl-1,2,4-triazine-3,5-di(thi)ones of the formula (Ia),

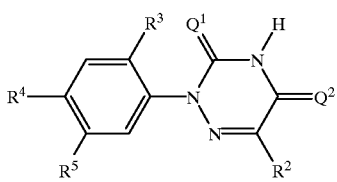 (Ia)

in which
$Q^1, Q^2, R^2, R^3, R^4$ and $R^5$ are each as defined above
are reacted with alkylating agents of the formula (IV), $R^1—X^2$ (IV)

in which
$R^1$ is as defined above and
$X^2$ represents halogen or the grouping —O—SO$_2$—O—R$^1$,
optionally in the presence of a diluent and optionally in the presence of a reaction auxiliary,
or that
(c) arylhydrazones of the formula (V),

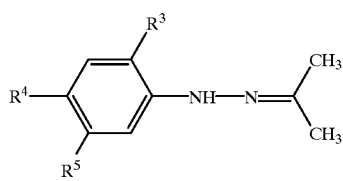 (V)

in which
$R^3, R^4$ and $R^5$ are each as defined above
are reacted with alkali metal (thio)cyanates of the formula (VI),

M—Q$^1$—CN (VI)

in which
$Q^1$ is as defined above and
M represents an alkali metal atom,
optionally in the presence of a diluent and optionally in the presence of a reaction auxiliary and the resulting 2-aryl-1,2,4-triazolidine-3-(thi)ones of the formula (VII),

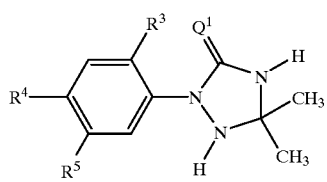 (VII)

in which
$Q^1 R^3, R^4$ and $R^5$ are each as defined above
are reacted with ketocarboxylic acids of the formula (VIII),

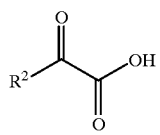 (VIII)

in which
$R^2$ is as defined above
optionally in the presence of a diluent and optionally in the presence of a reaction auxiliary,
or that (d) aryl-amines of the formula (IX),

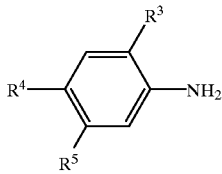
(IX)

in which $R^3$, $R^4$ and $R^5$ are each as defined above are diazotized and subsequently reacted with a cyanoacetylcarbamic acid ester of the formula (X),

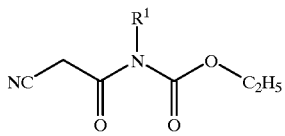
(X)

in which $R^1$ is as defined above, optionally in the presence of a diluent and optionally in the presence of a reaction auxiliary, and the resulting compounds of the formula (XI),

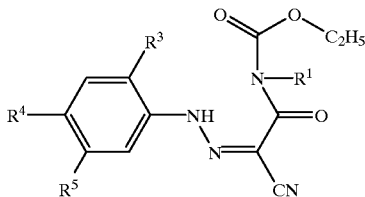
(XI)

in which $R^1$, $R^3$, $R^4$ and $R^5$ are each as defined above are cyclized optionally in the presence of a diluent and optionally in the presence of a reaction auxiliary, or that (e) arylhydrazines of the formula (XII)

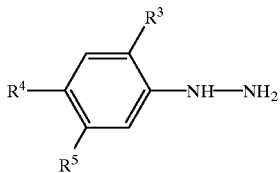
(XII)

in which $R^3$, $R^4$ and $R^5$ are each as defined above are reacted with ketocarboxylic acid derivatives of the formula (XIII),

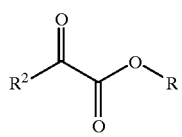
(XIII)

in which $R^2$ is as defined above and

R represents hydrogen or alkyl, optionally in the presence of a diluent and in the presence of a reaction auxiliary, and the resulting compounds of the formula (XIV)

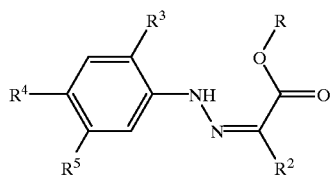
(XIV)

in which $R^2$, $R^3$, $R^4$ and $R^5$ are each as defined above and

R represents hydrogen or alkyl, are reacted, optionally in the presence of a diluent and optionally in the presence of a reaction auxiliary, with iso(thio)cyanates of the formula (XV), $$R^1\text{—}N\text{=}C\text{=}Q^1 \quad \text{(XV)}$$

in which $Q^1$ and $R^1$ are each as defined above, optionally in the presence of a diluent and optionally in the presence of a reaction auxiliary and the resulting compounds of the formula (XVI),

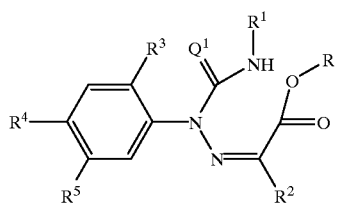
(XVI)

in which $Q^1$, $R^1$, $R^2$, $R^3$, $R^4$ and $R^5$ are each as defined above and R represents hydrogen or alkyl, are cyclized, optionally in the presence of a diluent and optionally in the presence of a reaction auxiliary, or that (f) 2-aryl-1,2,4-triazine-3,5-dione-6-carboxylic acids of the formula (XIX),

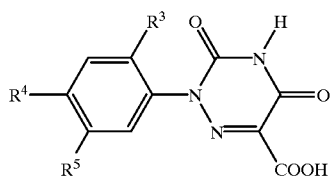
(XIX)

in which
R³, R⁴ and R⁵ are each as defined above are obtained,
if aryl-amines of the formula (IX),

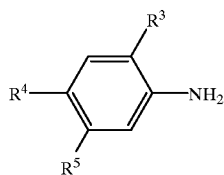
(IX)

in which
R³, R⁴ and R⁵ are each as defined above
are diazotized and subsequently reacted with the malonyldiurethane of the formula (XVII), $$CH_2(CO\text{---}NH\text{---}COOC_2H_5)_2 \qquad (XVII)$$

optionally in the presence of a diluent and optionally in the presence of a reaction auxiliary and subsequently cyclized.

4. A herbicidal composition comprising a herbicidally effective amount of a compound according to claim 1 and an extender.

5. A method of combating unwanted vegetation which comprises administering to such vegetation or to a locus from which it is desired to exclude such vegetation a herbicidally effective amount of a compound according to claim 1.

* * * * *